US010787651B2

(12) United States Patent
Yu et al.

(10) Patent No.: US 10,787,651 B2

(45) Date of Patent: Sep. 29, 2020

(54) BRADYRHIZOBIUM MONOOXYGENASE AND USE THEREOF FOR PREPARATION OF CHIRAL SULFOXIDE

(71) Applicants: JIANGSU AOSAIKANG PHARMACEUTICAL CO., LTD., Nanjing (CN); EAST CHINA UNIVERSITY OF SCIENCE AND TECHNOLOGY, Shanghai (CN)

(72) Inventors: Huilei Yu, Nanjing (CN); Yan Zhang, Nanjing (CN); Jianhe Xu, Nanjing (CN); Qian Zhao, Nanjing (CN); Jiang Pan, Nanjing (CN); Feng Liu, Nanjing (CN); Guoqiang Lin, Nanjing (CN)

(73) Assignees: JIANGSU AOSAIKANG PHARMACEUTICAL CO., LTD., Nanjing (CN); EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 16/620,525

(22) PCT Filed: Apr. 13, 2018

(86) PCT No.: PCT/CN2018/083060

§ 371 (c)(1),
(2) Date: Dec. 9, 2019

(87) PCT Pub. No.: WO2019/169695

PCT Pub. Date: Sep. 12, 2019

(65) Prior Publication Data

US 2020/0140830 A1 May 7, 2020

(30) Foreign Application Priority Data

Mar. 8, 2018 (CN) .......................... 2018 1 0191827

(51) Int. Cl.

| | |
|---|---|
| ***C12N 9/02*** | (2006.01) |
| ***C12P 17/02*** | (2006.01) |
| ***C12P 11/00*** | (2006.01) |
| ***C12P 17/10*** | (2006.01) |
| ***C12P 17/16*** | (2006.01) |
| *A61K 38/00* | (2006.01) |

(52) U.S. Cl.

CPC ............ *C12N 9/0073* (2013.01); *C12P 11/00* (2013.01); *C12P 17/10* (2013.01); *C12P 17/165* (2013.01)

(58) Field of Classification Search

None

See application file for complete search history.

(56) References Cited

U.S. PATENT DOCUMENTS 7,105,296 B2 * 9/2006 Bramucci ............... C12P 17/08 435/6.12

FOREIGN PATENT DOCUMENTS

| | | | |
|---|---|---|---|
| CN | 104017836 | A | 9/2014 |
| CN | 104560905 | A | 4/2015 |
| CN | 104673764 | A | 6/2015 |
| WO | 2011071982 | A2 | 6/2011 |

OTHER PUBLICATIONS

Okubo et al. (2013) Genome Analysis Suggests that the Soil Oligotrophic Bacterium Agromonas oligotrophica (Bradyrhizobium oligotrophicum) Is a Nitrogen-Fixing Symbiont of Aeschynomene indica, Appl. Environ. Microbiol., vol. 79, pp. 2542-2551.*

Okubo et al. (2011) Genome Analysis Suggests that the Soil Oligotrophic Bacterium Agromonas oligotrophica (Bradyrhizobium oligotrophicum) Is a Nitrogen-Fixing Symbiont of Aeschynonnene indica, Appl. Environ. Microbiol., vol. 79, No. 8, pp. 2541-2551.*

Wenjuan Tang, Isolation of phthalate esters degrading strains and biodegradation characteristics and whole genome analyses of *Rhizobium* sp. LMP-1, pp. 1-70.

Aitao Li, Screening and Utilization of Sulfide Monooxygenase Producing Strains, Chinese Doctoral Dissertations Full-Text Database, Dec. 30, 2011, pp. 1-118.

Okubo T. et al. , Genome analysis suggests that the soil oligotrophic bacterium Agromonas oligotrophica (Bradyrhizobium oligotrophicum) is a nitrogen-fixing symbiont of Aeschynomene indica, Appl. Environ. Microbiol. 79(8),2013, pp. 2542-2551.

Jian-Dong Zhang, et al., Synthesis of optically pure S-sulfoxide by *Escherichia coli* transformant cells coexpressing the P450 monooxygenase and glucose dehydrogenase genes, J Ind Microbiol Biotechnol, (2011) 38, pp. 633-641, DOI 10.1007/s10295-010-0809-3.

NCBI Reference Sequence: WP_015665598.1, NAD(P)/FAD-dependent oxidoreductase [Bradyrhizobium bligotrophicum], Dec. 5, 2017.

* cited by examiner

*Primary Examiner* — Manjunath N Rao

*Assistant Examiner* — Samuel W Liu

(74) *Attorney, Agent, or Firm* — Bayramoglu Law Offices LLC

(57) ABSTRACT

A *Bradyrhizobium* monooxygenase, a gene for encoding the monooxygenase, a recombinant expression vector comprising the gene and a recombinant transformant, a method of preparing the monooxygenase by the recombinant expression transformant, and a method of preparing an optically pure chiral sulfoxide by the monooxygenase, in particular to a method of preparing prazole drugs by means of catalyzing the asymmetric oxidation of thioether, a prazole precursor. As compared with other methods of preparing an optically pure sulfoxide, the product produced by the monooxygenase of the present invention as a catalyst has high optical purity, avoids the generation of the byproduct sulfone, and has advantages of mild reaction conditions, simple and convenient operations, easy amplification, etc.

4 Claims, 1 Drawing Sheet

Specification includes a Sequence Listing.

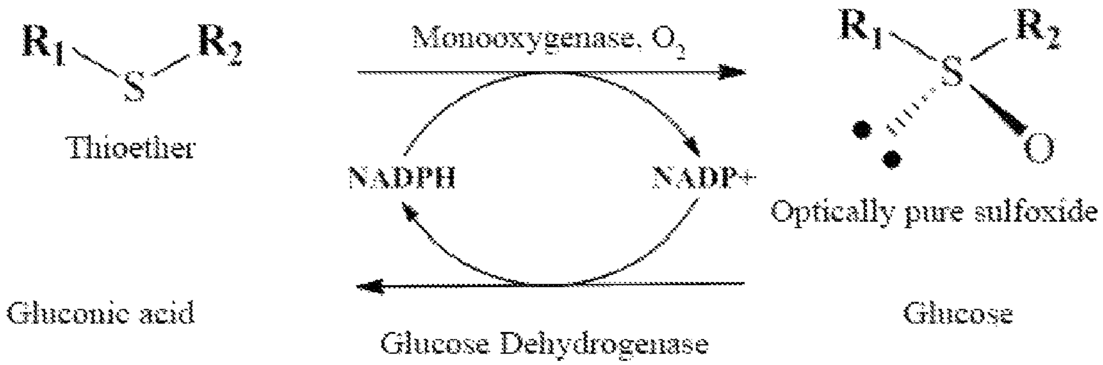
Thioether
Monooxygenase, $O_2$
NADPH
NADP+
Optically pure sulfoxide
Gluconic acid
Glucose
Glucose Dehydrogenase

BRADYRHIZOBIUM MONOOXYGENASE AND USE THEREOF FOR PREPARATION OF CHIRAL SULFOXIDE

CROSS REFERENCE TO RELATED APPLICATIONS

This application is the national phase entry of International Application No. PCT/CN2018/083060, filed on Apr. 13, 2018, which is based upon and claims priority to Chinese Patent Application No. 201810191827.3, filed on Mar. 8, 2018, the entire contents of which are incorporated herein by reference.

REFERENCE TO A "SEQUENCE LISTING"

An ASCII text file of Sequence Listing is submitted separately, naming "GBDF004_ST25_20200624-1830", created on 06/24/2020, and sized 10 KB, and the ASCII text file is incorporated herein by reference.

TECHNICAL FIELD

The present invention belongs to the field of bio-engineering technology. In particular, the present invention relates to a *Bradyrhizobium* monooxygenase, a gene for encoding the monooxygenase, a recombinant expression vector comprising the gene and a recombinant transformant, a method of preparing the monooxygenase by use of the recombinant expression transformant, and a method of preparing an optically pure chiral sulfoxide by use of the monooxygenase, especially a method of preparing prazole drugs by means of catalytic oxidation of thioether, a prazole precursor.

BACKGROUND

Chiral sulfoxides have a wide range of important application values. Their applications can be generally classified into several types: chiral auxiliaries, chiral ligands, chiral catalysts, and chiral drugs and drug intermediates.

Some chiral sulfoxides are important intermediates of drugs containing chiral center(s) of sulfur atom or the drug itself. For example, a series of benzopyrazole-based proton pump inhibitors (such as, esomeprazole) are chiral heterocyclyl sulfoxides. Proton Pump Inhibitors (PPIs) are the first choice drug for treating a variety of gastroesophageal diseases (e.g. gastric and duodenal ulcer, gastroesophageal reflex disease), which serve as $H^+/K^+$-ATPase inhibitors and have characteristics of quick effects, strong actions, high specificity, and long duration. Currently, the PPIs which are widely used in clinic comprise omeprazole (OME, launched in Sweden in 1988), lansoprazole (launched in Japan in 1995), pantoprazole (launched in Germany in 1997), rabeprazole (launched in the US in 1999), and esomeprazole (launched in the US in 2001). Of those, Lansoprazole (also known as Takepron, with a chemical name of 2-[3-methyl-4-(2,2,2-trifluoroethoxy)-2-piperdinyl]methylsulfinyl-1H-benzimidazole), which is a new generation of proton inhibitor-based anti-acid and anti-ulcer agents, effectively inhibits the gastric acid secretion. In clinic applications, lansoprazole exhibits a higher bioavailability than omeprazole, while the sustained release capsule containing pure dextrolansoprazole has better performances in terms of cure rate, duration of acid control, control rate of heartburn, and the like, as compared with racemic lansoprazole. The pure dextrolansoprazole was developed by Takeda Pharmaceutical Co. Ltd.

Japan, approved by the FDA in the US in 2009, and then successively went on sale in various countries in Europe, Asia, America, etc.

Bio-catalytic synthesis of chiral sulfoxides has advantages of high stereoselectivity, mild and safe reaction conditions, environmental friendliness, etc. and is a beneficial supplement to the chemical synthesis of chiral sulfoxide. With the development of bio-technology, it has currently become a research focus. Although there are numerous bio-catalysts capable of asymmetrically catalyzing the oxidation of thioethers, the existing bio-catalysts have poor catalytic efficiency on large hindered thioether substrates. Babiak et al. screened a wild type strain from soil pollutant, which was identified as *Lysinibacillus*. Cells grown by the strain was used to catalyze the conversion of omeprazole thioethers. When the substrate loading was 0.1 g/L, the conversion was only 77% after 48 fermentation cultivation. WO2011/071982 discloses that Codexis Company carried a directed evolution on cyclohexanone monooxygenase (CHMO) from *Acinetobacter* sp. NCIMB 9871, and the resultant engineered enzyme is capable of effectively catalyzing the oxidation of omeprazole thioether to prepare (S)-omeprazole. Nonetheless, there is still a lack of effective catalyst capable of asymmetrically catalyzing the oxidation of lansoprazole thioether. The engineered enzyme produced by Codexis Company can catalyze lansoprazole thioether to produce (R)-lansoprazole, but the catalytic effectiveness of the engineered enzyme is very low. When the substrate loading is 1.5 g/L, the conversion is merely 1.2% after 17 h, and the optical purity of the product cannot be determined due to the very low conversion.

Currently, dextrolansoprazole is still produced via chemical synthesis. In the current production, the process of asymmetric catalytic oxidation has a poor selectivity and a low conversion. The chiral metallic titanium reagents and auxiliary tartaric acid are used in large amounts, about 10-15% of thioether is left, and about 2% impurity of sulfone is produced. Due to the relatively large amount of impurities, the reaction product is required need to undergo multiple extraction and crystallization during the post-treatment profess. Thus, such process has a low yield, and will produce large amounts of three wastes (waste water, waste gas, and waste liquor). Meanwhile, the existing bio-catalysts require mild reaction conditions, and are safe and environmentally friendly, whereas they result in a low conversion.

SUMMARY

The present invention provides a *Bradyrhizobium oligotrophicum* ECU1212 obtained via screening to solve the problems of poor selectivity and low conversion of the chemical synthesis of sulfoxides and low conversion of the bio-catalytic synthesis of large hindered sulfoxides in the prior art.

The present invention provides a *Bradyrhizobium oligotrophicum*, which is *Bradyrhizobium oligotrophicum* ECU1212 deposited in the China General Microbiological Culture Collection Center under the CGMMC Accession No. CGMCC No. 15208.

In an embodiment, the *Bradyrhizobium oligotrophicum* can produce a *Bradyrhizobium oligotrophicum* ECU1212 thioether monooxygenase having an amino acid sequence as shown in SEQ ID No. 2.

The present invention further provides a monooxygenase comprising an amino acid sequence as shown in SEQ ID No.

2; or the monooxygenase comprises a mutant amino acid sequence generated by mutation of the amino acid sequence as shown in SEQ ID No. 2.

In an embodiment, the mutant amino acid sequence is a mutant amino acid sequence generated by the replacement of any one to five amino acids in the amino acid sequence as shown in SEQ ID No. 2.

In an embodiment, the mutant amino acid sequence is a mutant amino acid sequence generated by the replacement of any one or more amino acids at positions 295, 357, 394, 395, and 396 in the amino acid sequence as shown in SEQ ID No. 2.

In an embodiment, the mutant amino acid sequence comprises any one or more of the features of:

(1) replacing the amino acid Asp at position 295 with Cys in the amino acid sequence as shown in SEQ ID No. 2;

(2) replacing the amino acid Ser at position 357 with Ile in the amino acid sequence as shown in SEQ ID No. 2;

(3) replacing the amino acid Phe at position 394 with Ala in the amino acid sequence as shown in SEQ ID No. 2;

(4) replacing the amino acid Ser at position 395 with Leu in the amino acid sequence as shown in SEQ ID No. 2; and (5) replacing the amino acid Trp at position 396 with Ala in the amino acid sequence as shown in SEQ ID No. 2.

In an embodiment, the monooxygenase comprises a mutant amino acid sequence as shown in SEQ ID No. 4.

In an embodiment, the monooxygenase comprises a mutant amino acid sequence as shown in SEQ ID No. 6.

The present invention further provides an isolated nucleic acid for encoding any one of the foregoing monooxygenases.

The present invention further provides a recombinant expression vector comprising the foregoing nucleic acid.

The present invention further provides a recombinant expression transformant comprising the foregoing recombinant expression vector.

The present invention further provides a method of preparing the foregoing monooxygenase comprising of the step of:

culturing the foregoing recombinant expression transformant, followed by isolating the monooxygenase from the culture.

The present invention further provides use of the foregoing *Bradyrhizobium oligotrophicum* or monooxygenase in asymmetric catalytic oxidation of a prochiral thioether.

In an embodiment, the prochiral thioether compound is selected from compounds conforming to any one of the following formulae:

i.

(I)

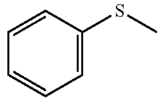

(II)

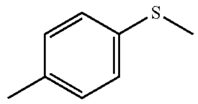

(III)

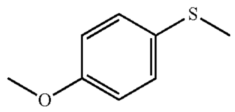

-continued

1.

(IV)

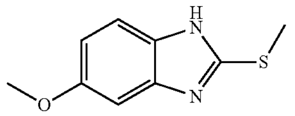

(V)

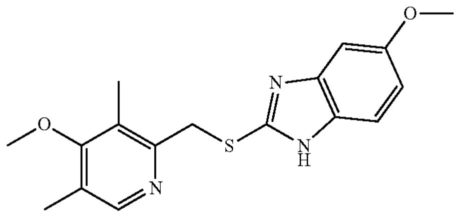

2.

(VI)

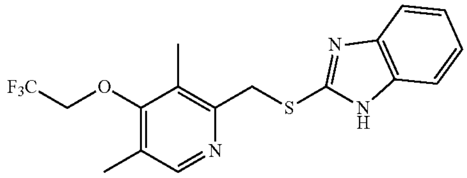

(VII)

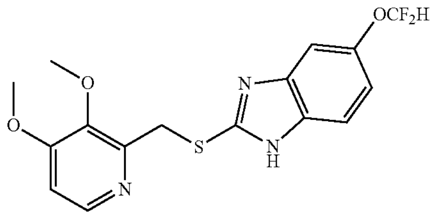

(VIII)

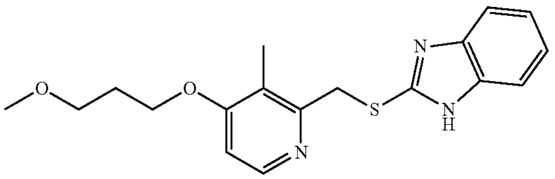

(IX)

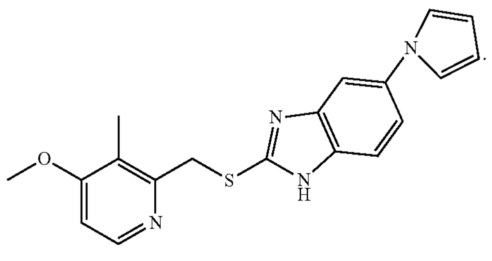

In an embodiment, the prochiral thioether compound is asymmetrically catalytically oxidized to sulfoxide.

The positive effect of the present invention relies on that the present invention provides a monooxygenase comprising BoTEMO or BoTEMO mutant which can effectively catalyze the asymmetric oxidation of thioether to prepare an optically pure chiral sulfoxide. When the concentration of lansoprazole thioether substrate is up to 10 g/L, the conversion is still above 99%, the ee value is above 99%, and the product sulfoxide would not be further oxidized to a byproduct sulfone. As compared with other asymmetric oxidation preparation methods, the product produced by the method of the present invention has high concentration and good optical purity. No byproduct is produced. The reaction requires mild conditions, is environmentally friendly, easy and convenient in operation, and easy to industrial amplification. Thus, it has good prospect in industrial application.

BRIEF DESCRIPTION OF DRAWINGS

FIGURE is a schematic view showing the reaction process of the asymmetrically catalytic oxidation of thioethers to prepare an optically pure chiral sulfoxide by use of the monooxygenase of the present invention.

DETAILED DESCRIPTION OF THE EMBODIMENTS

The *Bradyrhizobium oligotrophicum* as provided by the present invention is obtained by the inventor via large-scale soil microbial screening. Among others, the collection of soil is primarily divided into two types: directly collected soil samples and soil samples collected after embedding a substrate. There are total 252 soil samples. Focusing on lansoprazole thioether, the concentration of lansoprazole thioether was continuously increased by four rounds of gradient enrichment culture. By pre-screening and re-screening, a strain capable of catalyzing the oxidation of lansoprazole thioether was isolated from the soil, and designated as *Bradyrhizobium oligotrophicum* ECU1212. The designation was made in a manner of generic name (genus)+species name (species)+strain code, wherein *Bradyrhizobium* represents the generic name, *oligotrophicum* represents the species name, and ECU1212 represents the strain code.

At present, the *Bradyrhizobium oligotrophicum* has been deposited in the China General Microbiological Culture Collection Center, CGMCC (No. 3, Courtyyard 1, West Beichen Road, Chaoyang District, Beijing) at Jan. 15, 2018, under the Accession Number of CGMCC No. 15208.

The *Bradyrhizobium oligotrophicum* ECU1212 has the following physiological and biochemical characteristics:

The strain is rod-shaped when observed under a microscope, free of spores, Gram-negative, and aerobic. It is a strict respiratory type with oxygen as the terminal electron acceptor, and moves one polar flagellum or subpolar flagellumand. The colony is round, opaque, rare translucent, white and bossed, and has a granular structure. The optimum temperature of the strain is 25-30° C., and the optimum pH is 6.0-8.0. The colony would not exceed 1 mm after 5-7 days on yeast extract-mannitol-inorganic salt agar, and the liquid culture of 5-7 days or longer is moderately turbid.

The culturing method and condition of the *Bradyrhizobium oligotrophicum* ECU1212 are not specially restricted, as long as they can grow the strains of the *Bradyrhizobium oligotrophicum* ECU1212 and produce the monooxygenase of the present invention. A preferred media formula is: 1 g/L of peptone, 1 g/L broth extract, and 0.5 g/L of NaCl under the culture conditions of 28° C. Another preferred media formula is: 15 g/L of glucose, 5 g/L of peptone, 5 g/L of yeast powder, 0.5 g/L of $K_2HPO_4.3H_2O$, 0.5 g/L of $H_2PO_4$, 1.0 g/L of NaCl, 0.5 g/L of $MgSO_4$ under the culture condition of 28° C.

Optionally, resting cells harvested from the culture of *Bradyrhizobium oligotrophicum* ECU1212 are used to asymmetrically catalyze the oxidation of lansoprazole thioether to prepared (R)-lansoprazole under the conditions that the thioether substrate concentration is 0.1 g/L, the catalyst loading is 10 g/L, and the reaction is carried out at 30° C. under stirring at 180 rpm. The conversion rate of lansoprazole thioether can be up to 80%, and the optical purity can be up to 99% ee(R). it can be seen that the *Bradyrhizobium oligotrophicum* ECU1212 comprises functional enzyme(s) which serve to asymmetrically catalyze the oxidation and have a high catalytic conversion rate. Thus, it can solve the problem that the conventional bio-catalysts have low conversion rate in the asymmetric catalytic oxidation process.

In a further aspect, the *Bradyrhizobium oligotrophicum* ECU1212 according to the present invention can produce a monooxygenase comprising an amino acid sequence as shown in SEQ ID No. 2.

The inventor finds through experiments that the resting cells of *Bradyrhizobium oligotrophicum* ECU1212 is capable of asymmetrically catalyzing the oxidation of thioethers to produce sulfoxides, thereby indicating that the *Bradyrhizobium oligotrophicum* ECU1212 can produce an enzyme having the catalytic function, and has a gene encoding the enzyme. Thus, on the basis of the *Bradyrhizobium oligotrophicum* ECU1212, the present invention further provides a monooxygenase, as well as a method of preparing the monooxygenase and use of the monooxygenase, an isolated gene encoding the monooxygenase, a recombinant expression vector comprising the isolated gene, and a recombinant expression transformant, respectively.

Based on the screening of *Bradyrhizobium oligotrophicum* ECU1212, the inventor obtains the monooxygenase of the present invention by means of utilizing the strategy of bioinformatics analysis to analyze and predict the gene(s) of monooxygenase which may have significant oxidative activity on thioethers, sorting them for cloning and expression, and demonstrating the function(s) thereof. By using such method, a monooxygenase capable of effectively asymmetrically catalyzing the oxidation of thioether substrate to produce a chiral sulfoxide is obtained by cloning. The monooxygenase catalyzes the oxidation of five types of large hindered prazole thioether substrates with an ee value of up to 99%, and the product is determined to have an amino acid sequence as shown in SEQ ID No. 2. In the present invention, the monooxygenase is named as BoTEMO (*Bradyrhizobium oligotrophicum* ECU1212 Thioether Monooxygenase).

In a further aspect, the present invention can also mutate the amino acid sequence as shown in SEQ ID No. 2 to obtain a mutant amino acid sequence so as to modify the amino acid sequence as shown in SEQ ID No. 2, that is, modifying BoTEMO to produce a monooxygenase having improved activity. The modified BoTEMO is named as a BoTEMO mutant in the present invention, and comprises a mutant amino acid sequence generated by the mutation of the amino acid sequence as shown in SEQ ID No. 2.

Optionally, the BoTEMO is mutated by a random mutation strategy, and lansoprazole thioether is used as a screening substrate. After pre- and re-screening of the 10,000 mutant library, a derived protein having improved enzymatic activity—a BoTEMO mutant is obtained by the mutation (i.e. replacement, deletion, or addition of one or more amino acid) of the amino acid sequence as shown in SEQ ID No. 2.

The amino acid sequence of the mutated BoTEMO (i.e. the BoTEMO mutant) (namely, the mutant amino acid sequence generated by the mutation of the amino acid sequence as shown in SEQ ID No. 2, that is, the mutated amino acid sequence as compared with the amino acid sequence of BoTEMO) is preferably an amino acid sequence generated by replacing any one to five amino acids in the amino acid sequence as shown in SEQ ID No. 2.

In a further aspect, the amino acid sequence of the BoTEMO mutant is preferably an amino acid sequence generated by replacing one or more of the amino acids at positions 295, 357, 394, 395, and 396 of the amino acid sequence as shown in SEQ ID No. 2.

In a still further aspect, the amino acid sequence of the BoTEMO mutant is preferably an amino acid sequence generated by replacing one or more of the amino acids at positions 295, 395, and 396 of the amino acid sequence as shown in SEQ ID No. 2; or preferably an amino acid sequence generated by replacing one or both of the amino acids at positions 357 and 394 of the amino acid sequence as shown in SEQ ID No. 2.

For example, it is possible to replace Asp at position 295 with Cys in the amino acid sequence as shown in SEQ ID No. 2; Ser at position 357 with Ile in the amino acid sequence as shown in SEQ ID No. 2; Phe at position 394 with Ala in the amino acid sequence as shown in SEQ ID No. 2; Ser at position 395 with Leu in the amino acid sequence as shown in SEQ ID No. 2; or Trp at position 396 with Ala in the amino acid sequence as shown in SEQ ID No. 2.

Correspondingly, in accordance with the amino acid sequence of the BoTEMO mutant, persons skilled in the art can determine the nucleotide sequence encoding the corresponding BoTEMO mutant (that is, the nucleotide sequence corresponding to the amino acid sequence of the BoTEMO mutant) based on basic biological knowledge.

Optionally, the present invention further provides a BoTEMO mutant having improved activity which has an amino acid sequence as shown in SEQ ID No. 4. Correspondingly, the amino acid sequence is encoded by the nucleotide sequence as shown in SEQ ID No. 3.

Optionally, the present invention further provides a BoTEMO mutant having improved activity which has an amino acid sequence as shown in SEQ ID No. 6. correspondingly, the amino acid sequence is encoded by the nucleotide sequence as shown in SEQ ID No. 5.

It is note that the monooxygenase refers to any one or more of the BoTEMO or the BoTEMO mutants, unless specially indicated.

The present invention further provides an isolated gene comprising a nucleotide sequence as shown in SEQ ID No. 1; or a mutant nucleotide sequence generated by mutation of the nucleotide sequence as shown in SEQ ID No. Correspondingly, the foregoing isolated gene can encode the foregoing monooxygenase.

Optionally, the isolated gene encoding the BoTEMO of the present invention is derived by means of using the genomic DNA of *Bradyrhizobium oligotrophicum* ECU1212 as a template, utilizing conventional technical means in the art (such as, polymerase chain reaction, PCR) to obtain a complete DNA nucleotide molecule encoding the foregoing BoTEMO. And the primer pair of the isolated gene is designed and synthesized in accordance with genomic analysis.

Optionally, a forward primer and a reverse primer for preparing the primer pair of the foregoing isolated gene comprises the nucleotide sequences as follows:

```
Forward primer:
CCG CATATG TCAACTGAGCATGTCGAC,
and

Reverse primer:
CCG AAGCTT TCACGAATACCGCATCACCC,
```

wherein, the underlined portion in the forward primer is Nde I enzyme site, and the underlined portion in the reverse primer is Hind III enzyme site. Then, a PCR product of BOTEMO full-length gene is obtained through PCR gene amplification by using the genomic DNA of *Bradyrhizobium oligotrophicum* ECU1212 as a template. In particular, an isolated gene of the present invention has a nucleotide sequence as shown in SEQ ID No. 1, with a full length of 1461 bp. The start codon is ATG, the stop codon of TGA, and the coding sequences (CDS) begins with the $1^{st}$ base and ends with the $1461^{th}$ base. The encoded protein BoTEMO has an amino acid sequence as shown in SEQ ID No. 2.

In a further aspect, due to the degeneracy of codon, the nucleotide sequence encoding the amino acid sequence as shown in SEQ ID No. 2 is not restricted to the nucleotide sequence as shown in SEQ ID No. 1. Persons skilled in the art can obtain a mutant nucleotide sequence generated by the mutation of the nucleotide sequence as shown in SEQ ID No. 1 by means of properly introduction of replacement, deletion, modification, insertion, or addition. That is, the present invention encompasses those mutant nucleotide sequences, as long as the monooxygenase expressed thereby retains an activity of asymmetrically catalyzing the oxidation of thioethers.

The mutant nucleotide sequence generated by the mutation of the nucleotide sequence as shown SEQ ID No. 1 of the present invention can be prepared by the replacement, deletion, or addition of one or more nucleotides in the nucleotide sequence as shown in SEQ ID No. 1 under the premise of retaining the activity.

The nucleotide sequence as shown in SEQ ID No. 1 of the present invention can encode BoTEMO, and the mutant nucleotide sequence generated by the mutation of the nucleotide sequence as shown in SEQ ID No. 1 can encode any one of BoTEMO or BoTEMO mutant.

Correspondingly, the present invention further provides a recombinant expression vector comprising the foregoing isolated gene.

In particular and optionally, the recombinant expression vector can be constructed by through conventional means in the art by linking the nucleotide sequence of the isolated gene of the present invention to various appropriate vectors. Of those, the vectors can be a variety of conventional vectors in the art, such as, commercially available plasmids, cosmids, phages, or viral vectors, etc. In a further aspect, the vector is preferably a plasmid, and the recombinant expression vector prepared by conventional technical means in the art is a recombinant expression plasmid. More preferably, the plasmid is plasmid pET28a. The isolated gene of the present invention can be operably linked to express a suitable regulatory sequence so as to achieve a constitutive or an inducible expression of the monooxygenase.

Optionally, the recombinant expression vector of the present invention can be prepared by the following exemplary method: A PCR product comprising the isolated gene obtained by PCR amplification is subject to enzyme digestion with restriction endonucleases NdeI and HindIII to form complementary sticky ends, while a cloning vector gene fragment and an expression vector pET28a are subject to enzyme digestion with restriction endonucleases NdeI and HindIII, and the digested gene fragment and expression vector is linked with a ligase T4DNA to form a recombinant expression plasmid pET-BoTEMO comprising the isolated gene of the BoTEMO of the present invention.

Further correspondingly, the present invention further provides a recombinant expression transformant comprising the foregoing recombinant expression vector.

In particular and optionally, the recombinant expression transformant can be prepared by transforming the recombinant expression vector of the present invention into a host cell. Among others, the host cell can be various conventional host cells in the art, as long as the host cell can allow the recombinant expression vector to stably replicate itself, and the isolated gene of the monooxygenase carried by the host cell can be effectively expressed. In the present invention, it is preferably *Escherichia coli* (*E. coli*), more preferably *E. coli* BL21 (DE3) or *E. coli* DH5α.

Optionally, the recombinant expression plasmid pET-BoTEMO is transformed into *E. coli* BL21(DE3) to obtain the preferred gene engineering strain of the present invention, i.e. a recombinant *E. coli* BL21 (DE3)/pET-BoTEMO.

The method and conditions of culturing the recombinant expression transformant of the present invention are not particularly restricted, and can be properly selected according to common knowledge in the art in accordance with the different factors, such as, host cell types, culturing methods, and the like, as long as the recombinant expression transformant can grow and produce the monooxygenase of the present invention. If the recombinant expression transformant is *E. coli*, it is preferable to use an LB media comprising 10 g/L of peptone, 5 g/L of yeast extract, and 10 g/L of NaCl and having a pH of 7.0. It is preferably to culture the recombinant expression transformant and produce the monooxygenase as follows: The recombinant *E. coli* (preferably, *E. coli* BL21(DE3)) associated with the present invention is inoculated into an LB media containing kanamycin for culturing. When the optical density OD600 of the media solution reaches 0.5-0.7 (preferably, 0.6), it can effectively express the monooxygenase of the present invention under the induction of isopropyl-β-D-thiogalactopyranoside (IPTG) having a final concentration of 0.1-1.0 mmol/L (preferably, 0.2 mmol/L). The expressed monooxygenase can be separated by conventional biotechnology.

Namely, the present invention discloses a method of preparing the foregoing monooxygenase comprising culturing the foregoing recombinant expression transformant, followed by separating the monooxygenase from the culture.

The present invention further provides use of the foregoing *Bradyrhizobium oligotrophicum* ECU1212 or monooxygenase in asymmetrically catalyzing an oxidation of prochiral thioethers. Optionally, *Bradyrhizobium oligotrophicum* ECU1212 can be used in a form of its resting whole cells for asymmetrically catalyzing the oxidation of prochiral thioethers.

Further optionally, the prochiral thioethers are selected from compounds conforming to any formulae of:

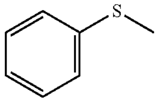
(I)

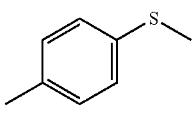
(II)

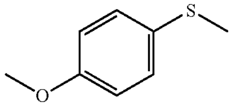
(III)

-continued

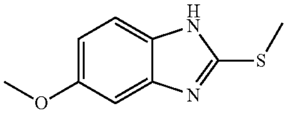
(IV)

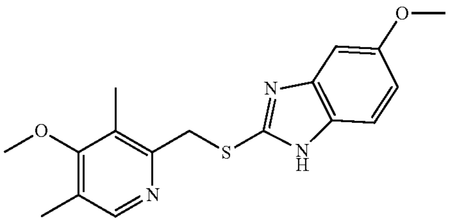
(V)

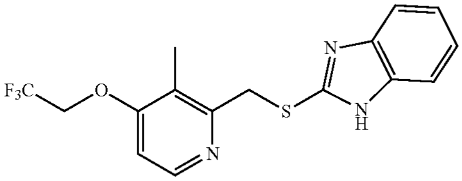
(VI)

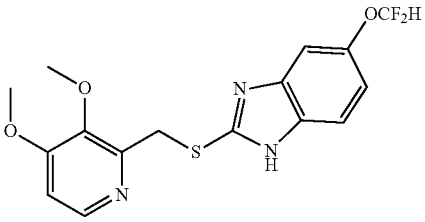
(VII)

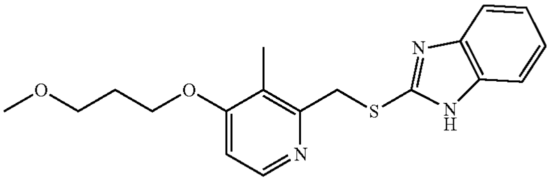
(VIII)

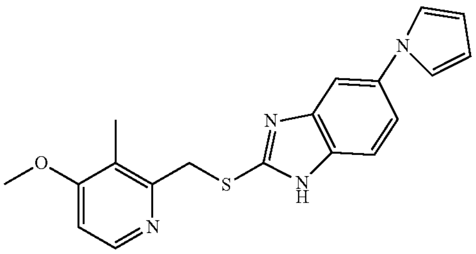
(IX)

Of those, the present invention describes the compounds of the foregoing formulae I to IX with their English names thioanisole, p-methyl thioanisole, p-methoxy thioanisole, 5-methoxy-2-(methylthio)benzimidazle, omeprazole thioether, lansoprazole thioether, pantoprazole thioether, rabeprazole thioether, ilaprazole thioether, respectively. Of course, these compounds can also be named in other ways in other literatures.

Further Optionally, the monooxygenase asymmetrically catalytically oxidizes the prochiral thioethers to sulfoxides.

Optionally, the *Bradyrhizobium oligotrophicum* ECU1212 or monooxygenase of the present invention is used to asymmetrically catalyze the oxidation of thioethers to generate optically active sulfoxides. The involved specific reaction conditions include substrate concentrations, pH, buffer concentrations, enzyme amounts, etc. which can be properly selected in accordance with conventional conditions of the reaction in the art. In a further aspect, the asymmetrically catalytic oxidation can be carried out under vibration or stirring conditions.

In particular, it can be carried out in line with the following exemplary process: As shown in the scheme in FIGURE, the reaction is performed at pH 8.0-10.0 in a Tris-HCl buffer having a concentration of 0.05-0.2 mol/L. In the presence of glucose dehydrogenase, glucose, and $NADP^+$, the thioether undergoes an asymmetrical oxidation under the action of the monooxygenase of the present invention to produce an optically active sulfoxide. It is preferable that the substrate has a concentration of 0.1-37 g/L in the reaction mixture. The enzyme activity unit (U) of the monooxygenase of the present invention is defined as the amount of enzyme required to catalyze 1 μmol substrate to generate a product per minute. During the asymmetrical oxidization of thioether, glucose and glucose dehydrogenase from *Bacillius megaterium* (prepared in accordance with the method as disclosed in Journal of Industrial Microbiology and Biotechnology 2011, 38, 633-641) are additionally added into the reaction system coenzyme recycling. By means of catalyzing the oxidation of glucose with glucose dehydrogenase, $NADP^+$ is transformed to NADPH. Depending on different reaction systems, the activity unit of glucose dehydrogenase is comparable to that of the monooxygenase of the present invention. The amount of glucose can be 2-20 mmol/L, and the amount of the additionally added $NADP^+$ can be 0-1 mmol/L. The asymmetrical oxidation can be carried out at a temperature of 20-35° C., preferably 25° C. After completion of the asymmetrical oxidation, the chiral sulfoxide product can be extracted from the reaction mixture in accordance with conventional methods of the present invention.

The *Bradyrhizobium oligotrophicum* ECU1212 of the present invention can produce a monooxygenase which can asymmetrically catalyze the oxidation of thioethers in an effectively manner to produce optically pure chiral sulfoxides, and has characteristics including high effectiveness, high stereoselectivity, and high conversion. For example, in the case that the substrate concentration of lansoprazole thioether is up to 10 g/L, the conversion rate can still reach 99% or above, the ee value reaches 99% or above, and the product sulfoxides would not be further oxidized to sulfone byproducts. As compared with other asymmetrical oxidation processes, the method of the present invention can produce a product having high concentration and good optical purity, and would not produce a byproduct. This method requires mild reaction conditions, are environmentally friendly, convenient in operation, easy to amplification, and thus has good prospect for industrial application.

Further, materials available from the following sources are used in the example of the present invention:

*Bradyrhizobium oligotrophicum* ECU1212, CGMCC No. 15208.

Expression plasmid pET28a, available from Shanghai Novagen Company.

*E. coli* DH5α and *E. coli* BL21 (DE3) competent cells, 2×Taq PCR MasterMix, agarose gel DNA extraction kit, all available from Tiangen Biotech (Beijing) Co. Ltd.

Unless otherwise indicated, the reagents and materials used in the present invention are all commercially available.

In the present specification, unless otherwise stated, the test methods in the examples are carried out in accordance with conventional methods and conditions or in line with the instructions of the reagents.

Example 1

Screening of *Bradyrhizobium oligotrophicum* ECU1212

The collection of soil is primarily divided into two types: directly collected soil samples and soil samples collected after embedding a substrate. There are total 252 soil samples.

Directly collected soil samples: Sampling was performed on relatively moist soil, such as, at the positions near water sources, plants, contaminated substrates, etc. About 3-5 g of soil was taken at 2-3 cm below the ground, and the used soil sample was stored at a low temperature in a dry place. Alternatively, the sample could be placed in 1.5 ml Eppendorf tube and stored in a 4° C. refrigerator. The collection samples included: Shanghai Fengxian Chemical Industrial zone, Xinhua Hospital, orchard, market, near dustbin, near river, green belts, campuses (Xuhui or Fengxian campus of East China University of Science and Technology), green spaces of residential areas, botanical garden, and the like.

Embedded substrate: Lansoprazole thioether is in white powder form, poorly soluble in water, but soluble in dimethylsulfoxide (DMSO). Thus, it is embedded at various positions in two different forms. The locations were generally selected as those having rich vegetation and microbial populations that had a potential to be acclimatized. One way was to directly embed the white powders at about 5 cm below the ground, and the other was to dissolve the lansoprazole thioether in DMSO, and then pour the solution onto the soil surface.

Prior to characterization of the selected strains and optimization of culture conditions, all the reactions were carried out at a temperature of 30° C. The media loading in a tube was 4 ml, and the rotate speed of shaking table was set at 180 rpm. The screen was carried out in four-round enrichment by means of gradient culture. That is, the concentration of yeast powder was halved and the concentration of the substrate was doubled in each round of culture. The plate culture was performed at 30° C. in an incubator.

Since the non-natural substrate lansoprazole thioether is difficult to use for most wild bacteria, only 124 samples of 252 soil samples were well grown after four rounds of enrichment. After pre-screening, it was found that 21 culture solutions contained the product lansoprazole, and the conversion rate reached 1%. From the pre-screened 21 culture solutions, 81 single strains were obtained by streaking. After solely cultured, the strains were subject to a conversion reaction a substrate concentration of 0.33 g/L for 24 h, and the strain having the most activity was subject to 16S rDNA verification. The sequencing results were searched in the NCBI database and compared with homologous sequences in the database. It was found that this strain had 99% sequence identity with *Bradyrhizobium oligotrophicum*. Thus, this strain was named as *Bradyrhizobium oligotrophicum* ECU1212.

Example 2

Preparation of Resting Cells of *Bradyrhizobium oligotrophicum* ECU1212

The *Bradyrhizobium oligotrophicum* ECU1212 screened in accordance with Example 1 was inoculated onto a rich media (glucose 15 g/L, peptone 10 g/L, yeast extract 5 g/L, $NaH_2PO_4$ 0.5 g/L, $MgSO_4$ 0.5 g/L, NaCl 10 g/L, pH 7.0), cultured at 28° C. at 180 rpm in a shaking table for 24, and centrifuged at 5000×g. The collected cells were refrigerated at −80° C. for 12 h, and freeze-dried in a freeze drier for 20 h to give lyophilized cells, which were stored at 4° C. in a refrigerator.

Example 3

Cloning of Isolated Gene of BoTEMO

Based on the screening of *Bradyrhizobium oligotrophicum* ECU1212, the invention utilizes the strategy of bioinformatics analysis to analyze and predict the gene(s) of enzyme which may have significant asymmetrically catalytic oxidative activity on thioethers, sorting them for cloning and expression, and demonstrating the function(s) thereof. By using such method, an isolated gene of BoTEMO capable of effectively asymmetrically catalyzing the oxidation of thioether substrate is cloned from the *Bradyrhizobium oligotrophicum* ECU1212.

The BoTEMO of the present invention (*Bradyrhizobium oligotrophicum* ECU1212 thioether monooxygenase) can catalyzes the oxidation of five types of high hindered prazole thioether substrates to produce products with an ee value of up to 99%. In comparison with conventional bio-catalysts, the present invention can substantially improve the optical purity of the product.

Optionally, the isolated gene of the BoTEMO of the present invention is preferably derived by means of utilizing the genomic DNA of *Bradyrhizobium oligotrophicum* ECU1212 as a template to obtain the whole nucleic acid molecule encoding the BoTEMO by conventional technology in the art (such as, polymerase chain reaction, PCR).

Optionally, in this example, the nucleotide sequences of the primer pair are as follows:

```
forward primer:
CCG CATATG TCAACTGAGCATGTCGAC,
and

reverse primer:
CCG AAGCTT TCACGAATACCGCATCACCC,
```

wherein the underlined portion in the forward primer is NdeI enzyme site, and the underlined portion in the reverse primer is HindIII enzyme site. By use of the genomic DNA of *Bradyrhizobium oligotrophicum* ECU1212 prepared in accordance with Example 1 as a template, a gene amplification is made by polymerase chain reaction (PCR).

Optionally, the PCR system comprises: 2×Taq PCR MasterMix 250, each of the forward and the reverse primers is 1.5 μl (0.3 μmol/L), DNA template 1.5 μl (0.1 μg), DMSO 2 and $ddH_2O$ 19 μl. The PCR amplification comprises the steps of: (1) pre-degeneration at 95° C. for 3 min; (2) degeneration at 94° C. for 1 min; (3) annealing at 55° C. for 30 s; (4) stretching at 72° C. for 2 min; repeating steps (2)-(4) for 30 times; (5) stretching at 72° C. for additional 10 min, and cooling to 12° C. The PCR product is purified through agarose gel electrophoresis, and recovered by use of an agarose gel DNA recovery kit for target band of 1400-1600 bp.

The isolated gene contained therein has a nucleotide sequence as shown in SEQ ID No. 1, with a full length of 1461 bp. The start codon is ATG, the stop codon of TGA, and the coding sequences (CDS) begins with the $1^{st}$ base and ends with the $1461^{th}$ base. The encoded protein BoTEMO has an amino acid sequence as shown in SEQ ID No. 2.

Example 4

Preparation of Recombinant Expression Plasmid and Recombinant Transformant

The PCT product comprising an isolated gene as cloned in accordance with the method of Example 3 was digested with restriction endonucleases NdeI and HindIII at 37° C. for 12 h. The reaction mixture was purified by agarose gel electrophoresis, and recovered with an agarose gel DNA recovery kit for target fragment. Under the action of $T_4$DNA ligase, the target fragment was linked with the plasmid pET28a (which is also subject to enzyme digestion with NdeI and HindIII) at 16° C. overnight to give a recombinant expression plasmid pET-BoTEMO.

The foregoing recombinant expression plasmid was transformed into competent cells of *E. coli* DH5α, and screened on a kanamycin-containing resistant plate for positive recombinants. Monoclonal population was picked, and testified by PCT analysis for positive clones. Monoclones were picked, and the colony PCR verified that they were positive clones. The recombinant bacteria were cultured. After plasmid amplification, plasmids were extracted, and retransformed into competent cells of *E. coli* BL21 (DE3). The transformant was applied onto a LB plate containing kanamycin which was inverted and cultured at 37° C. overnight to produce positive recombinant expression transformants *E. coli* BL21(DE3)/pET-BoTEMO. Colony PCR verified that they were positive clones.

Example 5

Expression of Recombinant BoTEMO

The recombinant expression transformants *E. coli* BL21 (DE3)/pET-BoTEMO were inoculated onto a LB media containing 50 μg/ml of kanamycin (peptone 10 g/L, yeast extract 5 g/L, NaCl 10 g/L, pH 7.0), and cultured at 37° C. at 180 rpm in a shaking table. When the OD600 of the culture reached 0.6, IPTG was added as the inducer to a final concentration of 0.2 mmol/L. After induction at 16° C. for 16 h, the culture was centrifuged. The cells were collected and washed twice with physiological saline to give resting cells. The resting cells obtained from 100 ml fermentation liquor were suspended in 10 ml buffer at pH 7.0, and subject to ultrasonication in an ice-water bath (the ultrasonic processor was set to run at 400 W, runs for 4 s, and suspends for 4 s, with total 99 cycles). The ultrasonication liquor was centrifuged at 4° C. in a refrigerated centrifuge at 15000 rpm for 40 min to give a supernatant crude enzyme solution liquor which was subject to activity measurement and protein purification.

The collected crude enzyme solution was refrigerated at −80° C. for 12 h, and then freeze-dried for in a vacuum freeze drier for 20 h to give lyophilized crude enzyme solution powders, which were stored at 4 4° C. in a refrigerator. The activity of lyophilized crude enzyme solution powders on thioanisole was 0.2 U/mg. The crude enzyme solution liquor was analyzed by polyacrylamide gel electrophoresis, and it was indicated that the recombinant protein was present in the cells in a partly soluble form, and moreover some proteins were present in the cell debris.

The purification experiments were all performed in a self-packing column with nickel affinity. The buffers used during the purification were as follows: Buffer A: 50 mM KPB, 500 mM NaCl, 10 mM imidazole, 2 mM β-mercaptoethanol, pH 8.0; Buffer B: 50 mM KPB, 500 mM NaCl, 300 mM imidazole, 2 mM β-mercaptoethanol, pH 8.0;

Buffer C: 50 mM KPB, 150 mM NaCl, 1 mM DTT, pH 9.0. The purification method was as follows:

1) The thallus was re-suspended in Buffer A and then subject to ultrasonication. The crude enzyme solution liquor after ultrasonication was centrifuged at 4° C. in a high-speed refrigerated centrifuge at 12000 rpm for 30 min. The centrifuged supernate was temporarily stored at 4° C. in a refrigerator or refrigerated storage.

2) The Ni column was pre-equilibrated with 5 to 10-fold column volumes of Buffer A.

3) The column was loaded with the stored supernate was loaded.

4) After completion of loading, the impurity protein was eluted with 5-10 fold column volume of a mixture of Buffers A and B (5% of Buffer B).

5) The target protein was eluted with one column volume of Buffer B and collected.

6) The collected target protein was concentrated by a 30 kDa ultrafiltration tube. When the mixture was concentrated to 500 μL, 5 ml of Buffer was added for further ultrafiltration concentration. The aforesaid process was repeated three to five times so as to remove the imidazole from the enzyme solution and reduce the salt level, thereby completing the substitution of buffer.

7) The enzyme solution after buffer substitution was quick-frozen in liquid nitrogen, and stored at −80° C. in a refrigerator.

Example 6

Determination of Activity of Recombinant BoTEMO and Glucose Dehydrogenase

The activity of BoTEMO and glucose dehydrogenase was determined by measuring the change of absorbance at 340 nm with a spectrophotometer.

The activity of BoTEMO was determined as follows. To 1 ml of the reaction system (100 mmol/L Tris-HCl buffer, pH 9.0) was added 1 mmol/L thioanisole and 0.2 mmol/L NADPH. The mixture was kept at 30° C. for 2 min, and then an appropriate amount of crude enzyme solution prepared in accordance with Example 5 was added. The mixture was rapidly mixed to uniform, and measured for the change of absorbance at 340 nm. The specific activity of the crude enzyme solution was determined as 101 mU/ml.

The activity of glucose dehydrogenase was determined as follows: To 1 ml of the reaction system (100 mmol/L sodium phosphate buffer, pH7.0) was added 10 mmol/L glucose and 1 mmol/L NADP'. The mixture was kept at 30° C. for 2 min, and then glucose dehydrogenase (prepared in accordance with the method as disclosed by: Journal of Industrial Microbiology and Biotechnology 2011, 38, 633-641). The mixture was rapidly mixed to uniform, and real-time measured for the change of absorbance at 340 nm.

The enzyme activity was calculated in accordance with the equation of:

$$\text{Enzyme Activity (U)}=EW\times V\times 10^3/(6220\times 1).$$

In the equation, EW represents the change of absorbance at 340 nm in 1 min; V represents the volume of the reaction mixture (in ml); 6220 represents the molar extinction coefficient of NADPH (in L/(mol·cm)); and 1 represents the optical path distance (in cm). Each unit of BoTEMO is defined as the enzyme amount required to catalyze the oxidation of 1 μmol NADPH per minute under the foregoing conditions. Each unit of glucose dehydrogenase is defined as the enzyme amount required to catalyze the reduction of 1 μmol $NADP^+$ per minute under the foregoing conditions.

Example 7

Determination of Activity of Recombinant BoTEMO Against a Series of Thioethers

To 0.5 ml of potassium phosphate buffer (100 mmol/L, pH 9.0) was added purified BoTEMO enzyme (purified BoTEMO enzyme prepared in accordance with the method of Example 5). A thioether substrate dissolved in DMSO was added so that the final concentration of the thioether was 0.2-2 mmol/L and the final concentration of DMSO was 2% (v/v), and NADPH was added to a final concentration 0.2-2 mmol/L. At 25° C., the reaction was stirred at 1000 rpm under shaking. After completion of reaction, 0.6 ml of ethyl acetate was added for extraction. The extract was dried over anhydrous sodium sulfate. The organic clear liquid was taken up, and evaporated overnight to remove the solvent. Then, the residue was dissolved with 0.5 ml of isopropanol and analyzed for measuring the ee value of product.

The particular analysis conditions of conversion rate and ee value of product are as follows:

The analysis is carried out with a high performance liquid chromatograph (HPLC) under the conditions of: a chiral OD-H column (250 mM×4.6 mm, 5 μm particle size, Daicel), a mobile phase of n-hexane:isopropanol=93:7, a flow rate of 1 ml/min, and UV detection at 254 nm; or an AS-H column (250 mm×4.6 mm, 5 μm particle size, Daicel), a mobile phase of n-hexane:isopropanol=55:45, a flow rate of 0.5 mL/min, and UV detection at 254 nm.

The activity of BoTEMO for catalyzing the asymmetrical oxidation of a series of thioether substrates to produce optically active sulfoxides was further determined by the method in accordance with Example. The results are shown in Table 1 below.

TABLE 1

Determination of Specific Activity of Purified BoTEMO Enzyme

| No. | Substrate | Column | Retention Time (min) | Specific Activity[a] | ee (%) |
|---|---|---|---|---|---|
| 1 | 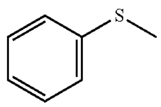 | OD-H | 4.31/19.9 (S) | +++ | 99 (S) |

TABLE 1-continued

| Determination of Specific Activity of Purified BoTEMO Enzyme | | | | | |
|---|---|---|---|---|---|
| No. | Substrate | Column | Retention Time (min) | Specific Activity[a] | ee (%) |
| 2 | 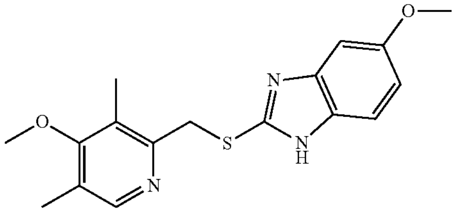 | AS-H | 9.23/15.8 (R) | ++ | 99 (R) |
| 3 | 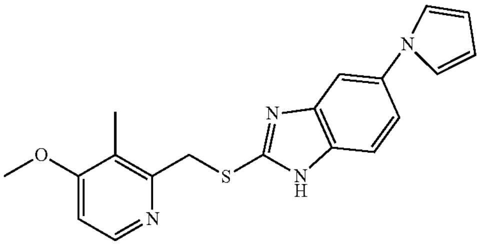 | AS-H | 12.6/16.4 (R) | ++ | 99 (R) |
| 4 | 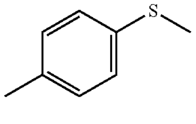 | OD-H | 3.11/15.5 (R)/ 18.5 (S) | + | 52 (R) |
| 5 | 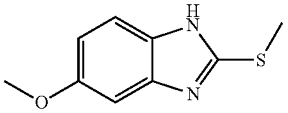 | AS-H | 7.62/12.4 (R) | + | 99 (R) |
| 6 | 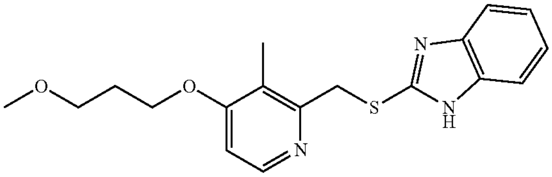 [SMILES: COCCCOc1ccnc(CSc2nc3ccccc3[nH]2)c1C] | AS-H | 10.2/12.5 (R) | + | 99 (R) |
| 7 | 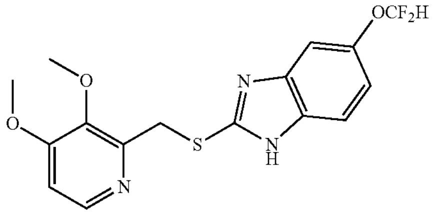 | AS-H | 10.7/23.6 (S) | + | 99 (S) |
| 8 | 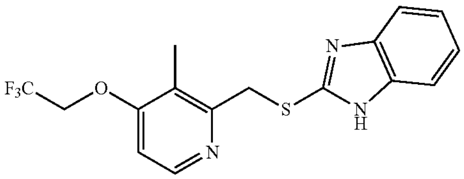 [SMILES: Cc1c(OCC(F)(F)F)ccnc1CSc1nc2ccccc2[nH]1] | AS-H | 10.7/15.9 (R) | + | 99 (R) |

[a]"+": <10 U/g; "++": 10 ~ 100 U/g; "+++": >100 U/g

Example 8

Whole *Bradyrhizobium oligotrophicum* ECU1212 resting cells asymmetrically catalyzed the oxidation of thioanisole.

To 100 ml Tris-HCl buffer (100 mmol/L, pH 9.0) was added 1 g of *Bradyrhizobium oligotrophicum* ECU1212 lyophilized cells (lyophilized cells prepared in accordance with Example 2), and thioanisole and methanol were added to a final concentration of 37 g/L, 10% (v/v). The reaction mixture was stirred at 28° C. and 180 rpm for reaction, and sampled with 100 μL at intervals. After sampling, 0.6 ml of ethyl acetate was added for extraction. The extract was dried over anhydrous sodium sulfate, and evaporated to remove the solvent. Then, the residue was dissolved in 0.5 ml isopropanol, and the solution was analyzed in accordance with the method of Example 7 for the conversion of reaction and the ee value of product. At 24 h, the conversion of reaction was above 99%, and the ee value of product was above 99% (S).

Example 9

Recombinant BoTEMO asymmetrically catalyzed the oxidation of thioanisole

To 0.5 ml potassium phosphate buffer (100 mmol/L, pH 9.0) was added 100 μL of crude enzyme solution of BoTEMO (the crude enzyme solution in accordance with the method of Example 5) and a crude enzyme solution of glucose dehydrogenase, and thioanisole, methanol, $NADP^+$ and glucose were added to the final concentration of 2 mmol/L, 10% (v/v), 0.2 mmol/L and 3.6 g/L, respectively. At 25° C. and 1000 rpm, the mixture was shaken for 1 h. After completion of reaction, 0.6 ml of ethyl acetate was added for extraction. The extract was dried over anhydrous sodium sulfate, and evaporated to remove the solvent. Then, the residue was dissolved in 0.5 ml of isopropanol. The mixture was analyzed in accordance with the method of Example 7 for measure the conversion of reaction and the ee value of product. The conversion of reaction was above 99%, and the ee value of product was above 99% (S).

Example 10

Recombinant BoTEMO asymmetrically catalyzed the oxidation of omeprazole thioether To 0.5 ml of potassium phosphate buffer (100 mmol/L, pH 9.0) was added 100 μL crude enzyme solution of BoTEMO (the crude enzyme solution prepared in accordance with the method of Example 5) and a crude enzyme solution of glucose dehydrogenase, and omeprazole thioether, methanol, $NADP^+$ and glucose were added to the final concentrations of 0.2 mmol/L, 10% (v/v), 0.2 mmol/L and 3.6 g/L, respectively. At 25° C. and 1000 rpm, the mixture was shaken for 1 h. After completion of reaction, 0.6 ml of ethyl acetate was added for extraction. The extract was dried over anhydrous sodium sulfate, and evaporated to remove the solvent. Then, the residue was dissolved in 0.5 ml isopropanol, and the solution was analyzed in accordance with the method of Example 7 for measuring the conversion of reaction and the ee value of product. The conversion of reaction was above 99%, and the ee value of product was above 99% (R).

Examples 11-15

Recombinant BoTEMO asymmetrically catalyzed the oxidation of a series of prazole thioethers.

To 10 ml of potassium phosphate buffer (100 mmol/L, pH 9.0) was added 0.1 g of lyophilized crude enzyme powders of BoTEMO (crude enzyme powders prepared in accordance with the method of Example 5) and 0.02 g of lyophilized crude enzyme powder of glucose dehydrogenase (15 U/mg), and 1-3 g/L of omeprazole thioether/lansoprazole thioether/pantoprazole thioether/rabeprazle thioether/ilaprazole thioether, 10% (v/v) of methanol, 0.2 mmol/L of $NADP^+$ and 10 g/L of glucose were added. The reaction was stirred at 25° C. and 180 rpm, and sampled with 100 μL at intervals. After sampling, 0.6 ml of ethyl acetate was added for extraction. The extract was dried over anhydrous sodium sulfate, and evaporated to remove the solvent. Then, the residue was dissolved in 0.5 ml of isopropanol, and the solution was analyzed in accordance with the method of Example 7 for measuring the conversion of reaction and the ee value of product.

When BoTEMO asymmetrically catalyzed the oxidation of five types of prazole precursor thioethers—large hindered thioethers—under the foregoing conditions, it was measured that the conversion of reaction was above 90% and the ee value of product was above 99% after 24 h reaction. The measurement results are listed in Table 2 below.

TABLE 2

| Example | Substrate | Substrate Loading (g/L) | Conversion (%) | ee (%) |
|---|---|---|---|---|
| 11 | 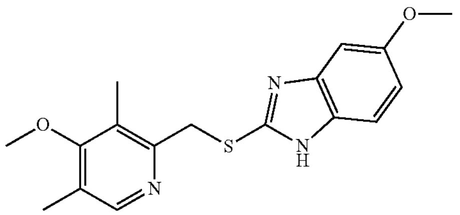 | 3 | 95 | 99 (R) |
| 12 | 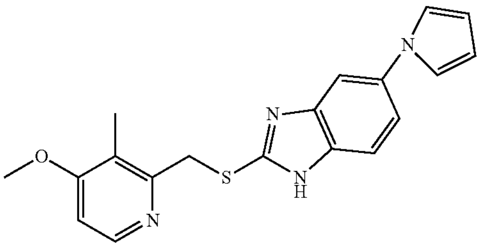 [SMILES: COc1ccnc(CSc2nc3cc(-n4cccc4)ccc3[nH]2)c1C] | 3 | 92 | 99 (R) |

TABLE 2-continued

| Example | Substrate | Substrate Loading (g/L) | Conversion (%) | ee (%) |
|---|---|---|---|---|
| 13 | 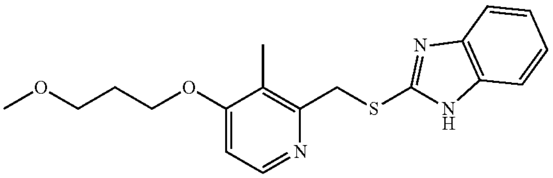 [SMILES: COCCCOc1ccnc(CSc2nc3ccccc3[nH]2)c1C] | 1 | 99 | 99 (R) |
| 14 | 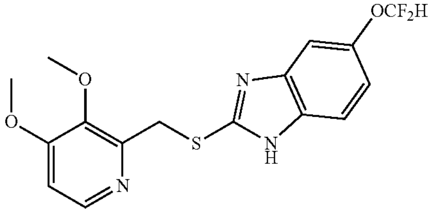 | 1 | 99 | 99 (S) |
| 15 | 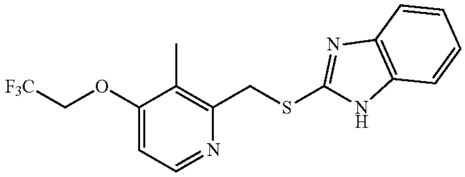 [SMILES: Cc1c(OCC(F)(F)F)ccnc1CSc1nc2ccccc2[nH]1] | 1 | 99 | 99 (R) |

Example 16

Recombinant BoTEMO asymmetrically catalyzed the oxidation of omeprazole thioether.

To 100 ml of Tris-HCl buffer (100 mmol/L, pH 9.0) was added 1 g of lyophilized crude enzyme powders of BoTEMO1 (crude enzyme powders prepared in accordance with the method of Example 5) and 0.2 g of crude enzyme powders of glucose dehydrogenase, and omeprazole thioether, methanol, $NADP^+$ and glucose were added to the final concentrations of 1 g/L, 10% (v/v), 0.2 mmol/L and 3.6 g/L, respectively. The reaction was stirred at 25° C. and 180 rpm. After 3 h reaction, the mixture was analyzed in accordance with the method of Example 7 for measuring the conversion of reaction and the ee value of product. The conversion of reaction was above 99%, and the ee value of product was above 99% (R).

Example 17

Recombinant BoTEMO asymmetrically catalyzed the oxidation of lansoprazole thioether.

To 10 ml of Tris-HCl buffer (100 mmol/L, pH 9.0) was added 0.2 g lyophilized crude enzyme powders of BoTEMO (crude enzyme powders prepared in accordance with the method of Example 5) and 0.02 g of lyophilized enzyme powders of glucose dehydrogenase. Lansoprazole thioether, methanol, $NADP^+$ and glucose were added to the final concentrations of 2 g/L, 10% (v/v), 0.2 mmol/L and 3.6 g/L, respectively. The reaction was stirred at 25° C. and 180 rpm for 24 h, and analyzed in accordance with the method of Example 7 for measuring the conversion of reaction and the ee value of product. When the lansoprazole thioether was asymmetrically catalytically oxidized to (R)-lansoprazole, the resultant conversion of reaction was above 99%, and the ee value of product was above 99% (R).

Example 18

Mutation of BoTEMO

The BoTEMO full-length gene sequence (such as, the nucleotide sequence as shown in SEQ ID NO. 1) prepared in accordance with Example 3 was subject to site-directed mutagenesis to give two mutants:

(1) By mutating G to T at position 883, A to G at position 884, C to T at position 1184, T to G at position 1186, and G to C at position 1187 in the nucleotide sequence encoding the BoTEMO, a mutant nucleotide sequence as shown in SEQ ID No. 3 is obtained. The amino acid sequence encoded thereby is that shown in SEQ ID No. 4, i.e. the amino acid sequence obtained by mutating Asp to Cys at position 295, Ser to Leu at position 395, and Trp to Ala at position 396 in BoTEMO (the amino acid sequence as shown in SEQ ID No. 2). The monooxygenase encoded by this mutant gene is named as BoTEMO-M1 (the amino acid sequence as shown in SEQ ID No. 4).

(2) By mutating G to T at position 1070, T to G at position 1180, T to C at position 1181, and C to A at position 1182 in the nucleotide sequence encoding the BoTEMO, the nucleotide sequence of the mutant gene as shown in SEQ ID No. 5 is obtained. The amino acid sequence encoded thereby is shown in SEQ ID No. 6, i.e. the amino acid sequence obtained by mutating Ser to Ile at position 357 and Phe to Ala at position 394 in the BoTEMO (the amino acid sequence as shown in SEQ ID No. 2). The monooxygenase encoded by this mutant gene is named as BoTEMO-M2 (the amino acid sequence as shown in SEQ ID No. 6).

Recombinant transformants were prepared from the foregoing two mutant genes of BoTEMO-M1 and BoTEMO-M2 in accordance with the method of Example 4. Resting cells and lyophilized crude enzyme powders were prepared in accordance with the method of Example 5. And further, the enzyme activities of BoTEMO-M1 and BoTEMO-M2 powders were measured in accordance with the method of measuring the enzyme activity of Example 6. The enzyme activities of BoTEMO-M1 and BoTEMO-M2 are 7.6 times that of BoTEMO (BoTEMO-M1) and 1.6 times (BoTEMO-M2), respectively. The activity against the lansoprazole thioether reaches 20 U/g (BoTEMO-M1) and 4.2 U/g (BoTEMO-M2).

Example 19

BoTEMO-M1 asymmetrically catalyzed the oxidation of lansoprazole thioether.

To 100 ml Tris-HCl buffer (100 mmol/L, pH 9.0) was added 1 g of lyophilized crude enzyme powders of BoTEMO-M1 and 0.2 g crude enzyme of glucose dehydrogenase. Lansoprazole thioether, methanol, $NADP^+$ and glucose were added to the final concentrations of 10 g/L, 10% (v/v), 0.2 mmol/L and 15 g/L, respectively. The reaction was stirred at 25° C. and 180 rpm for 24 h. When the lansoprazole thioether was asymmetrically catalytically oxidized to (R)-lansoprazole, the resultant conversion of the reaction was above 99%, and the ee value of product was above 99% (R).

Example 20

BoTEMO-M2 asymmetrically catalyzed the oxidation of lansoprazole thioether.

To 100 ml Tris-HCl buffer (100 mmol/L, pH 9.0) was added lyophilized crude enzyme powders of BoTEMO-M2 and 0.2 g crude enzyme of glucose dehydrogenase. Lansoprazole thioether, methanol, $NADP^+$ and glucose were added to the final concentrations of 3 g/L, 10% (v/v), 0.2 mmol/L and 5.4 g/L, respectively. The reaction was stirred at 25° C. and 180 rpm for 24 h. When the lansoprazole thioether was asymmetrically catalytically oxidized to (R)-lansoprazole, the resultant conversion of the reaction was above 99%, and the ee value of product was above 99% (R).

Example 21

BoTEMO-M1 asymmetrically catalyzed the oxidation of lansoprazole thioether.

To 2 L Tris-HCl buffer (100 mmol/L, pH 9.0) was added 20 g lyophilized crude enzyme powders of BoTEMO-M1 and 4 g crude enzyme of glucose dehydrogenase. Lansoprazole thioether, methanol, $NADP^+$ and glucose were added to the final concentrations of 10 g/L, 10% (v/v), 0.2 mmol/L and 15 g/L, respectively. The reaction was stirred at 25° C. and 180 rpm for 24 h. When the lansoprazole thioether was asymmetrically catalytically oxidized to (R)-lansoprazole, the resultant conversion of the reaction was above 99%, and the ee value of product was above 99% (R). Separation by extraction gave 17.2 g of the product (R)-lansoprazole, and the yield was 86%.

It is to be understood that persons skilled in the art may make various changes and modifications to the present invention upon reading the foregoing contents of the present invention, and such equivalents are also encompassed within the scope as defined by the appended claims of the present application.

What is claimed is:

1. An engineered and isolated monooxygenase, wherein the monooxygenase is capable of asymmetrically catalyzing an oxidation of prochiral thioethers, and the monooxygenase comprises the amino acid sequence of SEQ ID NO: 4.

2. A method of oxidizing a prochiral thioether, comprising the step of applying the monooxygenase of claim 1 in asymmetric catalytic oxidation of the prochiral thioether.

3. The method according to claim 2, wherein, the prochiral thioether is selected from the group consisting of the compounds having the formulas of (I)-(IX):

(I)

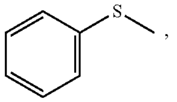

(II)

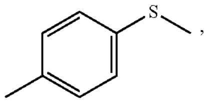

(III)

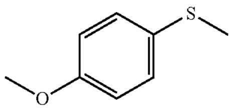

(IV)

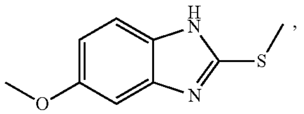

(V)

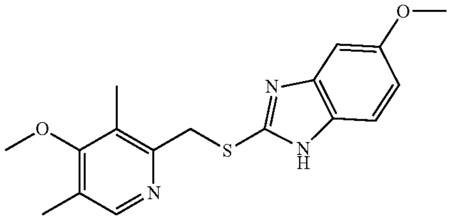

-continued (VI)

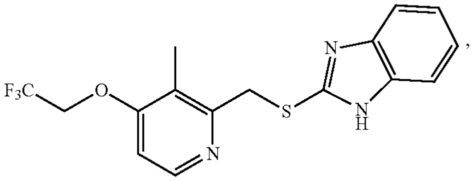

(VII)

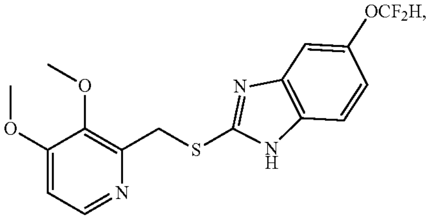

(VIII)

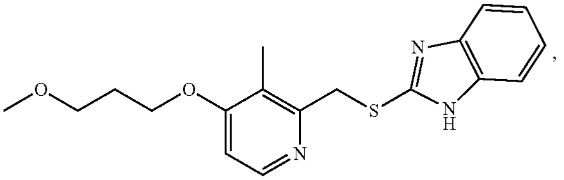

and (IX)

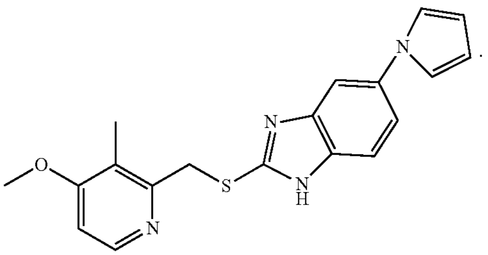

4. The method according to claim 2, wherein the prochiral thioether is asymmetrically catalytically oxidized to sulfoxide.

* * * * *

SEQUENCE LISTING

```
<160> NUMBER OF SEQ ID NOS: 8

<210> SEQ ID NO 1
<211> LENGTH: 1461
<212> TYPE: DNA
<213> ORGANISM: Bradyrhizobium oligotrophicum ECU1212

<400> SEQUENCE: 1

atgtcaactg agcatgtcga cgtgctgatc gtcggtgccg ggctgtccgg catcgccgcc      60

gcctatcatc tgcagcacaa atgtccgggc aagcgcttcg ccctcctgga ggggcgcggt     120

gcgctcggcg gcacctggga cctgttccgc tatcccggca tccgctcgga cagcgacatg     180

tacacgctcg gctattcgtt caagccgtgg accgatccga aagccatcgc cgacgggccg     240

cagatcctca aatatgtcca ggacaccgcg accgagaacg gcatcgaccg ccacatccgt     300

ttcaatcatc gcgtccgccg cgcctcgtgg tcgagcgcgg acgcacgctg gacggtcgag     360

gccgagcggc agacggcgca gggcacgacg gaaaccgtgt cgatgacatg cggcttcctt     420

ttcatgtgct ccggctacta ccgctatgag aaaggctatc tgccggactt caagggcatg     480

gccgatttca agggccgcat cgtgcatccg caggcctggc ccgccgacct cgactatgcc     540

ggcaaacgcg tcgtcgtgat cggctccggt gcgacggcgg tgacgctggt gccggcaatg     600

gccaagaccg cggcgcacgt gacgatgctg cagcgctcgc cgacctatgt cgtgtcgcgc     660

ccggcgcagg atgcgctcgc caacaagctg cgcgagcacc tcccggctgg tctcgcctat     720

catctgatcc gctggcgcaa cgtgctgttc gggatgtatt tcttccagct cagccgccgc     780

aagccgcagc gggtcaagca gctgatatta gggggcgtgc gcgccgcgct tggccccgac     840

tacgacgtcg ccacccattt cacgccgcgc tacaacccgt gggaccagcg gttgtgcctg     900

gtgccggatg gcgacctgtt caggaccatc cgcgagcagc gggcgtcggt ggtgacagcc     960
```

-continued

```
gggatcgaca cgttcaccga gcgcggcctg cgcctctccg acggccgcga gctcgaggcc   1020

gaaatcgtgg tgaccgcgac ggggctggtg ctgcaggttc tcggcggcag cgaggtcgtg   1080

gtcgacggcc gcacggtcga ttttgccaag acgctcaact acaagggcat gatgtattcc   1140

gacgtgccca acatggcggc caccctcggc tacacgaact tctcgtggac gctgaaatgc   1200

gatctcacct gcgaatatgt ctgccgtctc ctcaactaca tggatcgcca tggctatcgc   1260

caatgcgtgc cgcacaacga cgacaccacc gtcacgccgc tgccgtcgct gagcttcagc   1320

tccggctatg tgcagcgctc gattgccgac ctgcccaagc aaggctcgaa gcggccgtgg   1380

cggctgtacc agaactacgc gctggatatc gtctcgctgc ggttcggcaa ggtcgatgat   1440

ggggtgatgc ggtattcgtg a                                              1461


<210> SEQ ID NO 2
<211> LENGTH: 486
<212> TYPE: PRT
<213> ORGANISM: Bradyrhizobium oligotrophicum ECU1212

<400> SEQUENCE: 2

Met Ser Thr Glu His Val Asp Val Leu Ile Val Gly Ala Gly Leu Ser
1               5                   10                  15

Gly Ile Ala Ala Ala Tyr His Leu Gln His Lys Cys Pro Gly Lys Arg
            20                  25                  30

Phe Ala Leu Leu Glu Gly Arg Gly Ala Leu Gly Gly Thr Trp Asp Leu
        35                  40                  45

Phe Arg Tyr Pro Gly Ile Arg Ser Asp Ser Asp Met Tyr Thr Leu Gly
    50                  55                  60

Tyr Ser Phe Lys Pro Trp Thr Asp Pro Lys Ala Ile Ala Asp Gly Pro
65                  70                  75                  80

Gln Ile Leu Lys Tyr Val Gln Asp Thr Ala Thr Glu Asn Gly Ile Asp
                85                  90                  95

Arg His Ile Arg Phe Asn His Arg Val Arg Arg Ala Ser Trp Ser Ser
            100                 105                 110

Ala Asp Ala Arg Trp Thr Val Glu Ala Glu Arg Gln Thr Ala Gln Gly
        115                 120                 125

Thr Thr Glu Thr Val Ser Met Thr Cys Gly Phe Leu Phe Met Cys Ser
    130                 135                 140

Gly Tyr Tyr Arg Tyr Glu Lys Gly Tyr Leu Pro Asp Phe Lys Gly Met
145                 150                 155                 160

Ala Asp Phe Lys Gly Arg Ile Val His Pro Gln Ala Trp Pro Ala Asp
                165                 170                 175

Leu Asp Tyr Ala Gly Lys Arg Val Val Val Ile Gly Ser Gly Ala Thr
            180                 185                 190

Ala Val Thr Leu Val Pro Ala Met Ala Lys Thr Ala Ala His Val Thr
        195                 200                 205

Met Leu Gln Arg Ser Pro Thr Tyr Val Val Ser Arg Pro Ala Gln Asp
    210                 215                 220

Ala Leu Ala Asn Lys Leu Arg Glu His Leu Pro Ala Gly Leu Ala Tyr
225                 230                 235                 240

His Leu Ile Arg Trp Arg Asn Val Leu Phe Gly Met Tyr Phe Phe Gln
                245                 250                 255

Leu Ser Arg Arg Lys Pro Gln Arg Val Lys Gln Leu Ile Leu Gly Gly
            260                 265                 270

Val Arg Ala Ala Leu Gly Pro Asp Tyr Asp Val Ala Thr His Phe Thr
```

-continued

```
        275                 280                 285

Pro Arg Tyr Asn Pro Trp Asp Gln Arg Leu Cys Leu Val Pro Asp Gly
    290                 295                 300

Asp Leu Phe Arg Thr Ile Arg Glu Gln Arg Ala Ser Val Val Thr Ala
305                 310                 315                 320

Gly Ile Asp Thr Phe Thr Glu Arg Gly Leu Arg Leu Ser Asp Gly Arg
                325                 330                 335

Glu Leu Glu Ala Glu Ile Val Val Thr Ala Thr Gly Leu Val Leu Gln
            340                 345                 350

Val Leu Gly Gly Ser Glu Val Val Val Asp Gly Arg Thr Val Asp Phe
        355                 360                 365

Ala Lys Thr Leu Asn Tyr Lys Gly Met Met Tyr Ser Asp Val Pro Asn
    370                 375                 380

Met Ala Ala Thr Leu Gly Tyr Thr Asn Phe Ser Trp Thr Leu Lys Cys
385                 390                 395                 400

Asp Leu Thr Cys Glu Tyr Val Cys Arg Leu Leu Asn Tyr Met Asp Arg
                405                 410                 415

His Gly Tyr Arg Gln Cys Val Pro His Asn Asp Asp Thr Thr Val Thr
            420                 425                 430

Pro Leu Pro Ser Leu Ser Phe Ser Ser Gly Tyr Val Gln Arg Ser Ile
        435                 440                 445

Ala Asp Leu Pro Lys Gln Gly Ser Lys Arg Pro Trp Arg Leu Tyr Gln
    450                 455                 460

Asn Tyr Ala Leu Asp Ile Val Ser Leu Arg Phe Gly Lys Val Asp Asp
465                 470                 475                 480

Gly Val Met Arg Tyr Ser
                485


<210> SEQ ID NO 3
<211> LENGTH: 1461
<212> TYPE: DNA
<213> ORGANISM: Artificial Sequence
<220> FEATURE:
<223> OTHER INFORMATION: variation

<400> SEQUENCE: 3

atgtcaactg agcatgtcga cgtgctgatc gtcggtgccg ggctgtccgg catcgccgcc      60

gcctatcatc tgcagcacaa atgtccgggc aagcgcttcg ccctcctgga ggggcgcggt     120

gcgctcggcg gcacctggga cctgttccgc tatcccggca tccgctcgga cagcgacatg     180

tacacgctcg gctattcgtt caagccgtgg accgatccga aagccatcgc cgacgggccg     240

cagatcctca aatatgtcca ggacaccgcg accgagaacg gcatcgaccg ccacatccgt     300

ttcaatcatc gcgtccgccg cgcctcgtgg tcgagcgcgg acgcacgctg gacggtcgag     360

gccgagcggc agacggcgca gggcacgacg gaaaccgtgt cgatgacatg cggcttcctt     420

ttcatgtgct ccggctacta ccgctatgag aaaggctatc tgccggactt caagggcatg     480

gccgatttca agggccgcat cgtgcatccg caggcctggc ccgccgacct cgactatgcc     540

ggcaaacgcg tcgtcgtgat cggctccggt gcgacggcgg tgacgctggt gccggcaatg     600

gccaagaccg cggcgcacgt gacgatgctg cagcgctcgc cgacctatgt cgtgtcgcgc     660

ccggcgcagg atgcgctcgc caacaagctg cgcgagcacc tcccggctgg tctcgcctat     720

catctgatcc gctggcgcaa cgtgctgttc gggatgtatt tcttccagct cagccgccgc     780

aagccgcagc gggtcaagca gctgatatta gggggcgtgc gcgccgcgct tggccccgac     840
```

-continued tacgacgtcg ccacccattt cacgccgcgc tacaacccgt ggtgccagcg gttgtgcctg 900
gtgccggatg gcgacctgtt caggaccatc cgcgagcagc gggcgtcggt ggtgacagcc 960
gggatcgaca cgttcaccga gcgcggcctg cgcctctccg acggccgcga gctcgaggcc 1020
gaaatcgtgg tgaccgcgac ggggctggtg ctgcaggttc tcggcggcat cgaggtcgtg 1080
gtcgacggcc gcacggtcga ttttgccaag acgctcaact acaagggcat gatgtattcc 1140
gacgtgccca acatggcggc caccctcggc tacacgaacg cattggcgac gctgaaatgc 1200
gatctcacct gcgaatatgt ctgccgtctc ctcaactaca tggatcgcca tggctatcgc 1260
caatgcgtgc cgcacaacga cgacaccacc gtcacgccgc tgccgtcgct gagcttcagc 1320
tccggctatg tgcagcgctc gattgccgac ctgcccaagc aaggctcgaa gcggccgtgg 1380
cggctgtacc agaactacgc gctggatatc gtctcgctgc ggttcggcaa ggtcgatgat 1440
ggggtgatgc ggtattcgtg a 1461

<210> SEQ ID NO 4
<211> LENGTH: 486
<212> TYPE: PRT
<213> ORGANISM: Artificial Sequence
<220> FEATURE:
<223> OTHER INFORMATION: VARIANT

<400> SEQUENCE: 4

Met Ser Thr Glu His Val Asp Val Leu Ile Val Gly Ala Gly Leu Ser
1 5 10 15

Gly Ile Ala Ala Ala Tyr His Leu Gln His Lys Cys Pro Gly Lys Arg
20 25 30

Phe Ala Leu Leu Glu Gly Arg Gly Ala Leu Gly Gly Thr Trp Asp Leu
35 40 45

Phe Arg Tyr Pro Gly Ile Arg Ser Asp Ser Asp Met Tyr Thr Leu Gly
50 55 60

Tyr Ser Phe Lys Pro Trp Thr Asp Pro Lys Ala Ile Ala Asp Gly Pro
65 70 75 80

Gln Ile Leu Lys Tyr Val Gln Asp Thr Ala Thr Glu Asn Gly Ile Asp
85 90 95

Arg His Ile Arg Phe Asn His Arg Val Arg Arg Ala Ser Trp Ser Ser
100 105 110

Ala Asp Ala Arg Trp Thr Val Glu Ala Glu Arg Gln Thr Ala Gln Gly
115 120 125

Thr Thr Glu Thr Val Ser Met Thr Cys Gly Phe Leu Phe Met Cys Ser
130 135 140

Gly Tyr Tyr Arg Tyr Glu Lys Gly Tyr Leu Pro Asp Phe Lys Gly Met
145 150 155 160

Ala Asp Phe Lys Gly Arg Ile Val His Pro Gln Ala Trp Pro Ala Asp
165 170 175

Leu Asp Tyr Ala Gly Lys Arg Val Val Val Ile Gly Ser Gly Ala Thr
180 185 190

Ala Val Thr Leu Val Pro Ala Met Ala Lys Thr Ala Ala His Val Thr
195 200 205

Met Leu Gln Arg Ser Pro Thr Tyr Val Val Ser Arg Pro Ala Gln Asp
210 215 220

Ala Leu Ala Asn Lys Leu Arg Glu His Leu Pro Ala Gly Leu Ala Tyr
225 230 235 240

His Leu Ile Arg Trp Arg Asn Val Leu Phe Gly Met Tyr Phe Phe Gln
245 250 255

-continued

```
Leu Ser Arg Arg Lys Pro Gln Arg Val Lys Gln Leu Ile Leu Gly Gly
            260                 265                 270

Val Arg Ala Ala Leu Gly Pro Asp Tyr Asp Val Ala Thr His Phe Thr
        275                 280                 285

Pro Arg Tyr Asn Pro Trp Cys Gln Arg Leu Cys Leu Val Pro Asp Gly
    290                 295                 300

Asp Leu Phe Arg Thr Ile Arg Glu Gln Arg Ala Ser Val Val Thr Ala
305                 310                 315                 320

Gly Ile Asp Thr Phe Thr Glu Arg Gly Leu Arg Leu Ser Asp Gly Arg
                325                 330                 335

Glu Leu Glu Ala Glu Ile Val Val Thr Ala Thr Gly Leu Val Leu Gln
            340                 345                 350

Val Leu Gly Gly Ser Glu Val Val Val Asp Gly Arg Thr Val Asp Phe
        355                 360                 365

Ala Lys Thr Leu Asn Tyr Lys Gly Met Met Tyr Ser Asp Val Pro Asn
    370                 375                 380

Met Ala Ala Thr Leu Gly Tyr Thr Asn Phe Leu Ala Thr Leu Lys Cys
385                 390                 395                 400

Asp Leu Thr Cys Glu Tyr Val Cys Arg Leu Leu Asn Tyr Met Asp Arg
                405                 410                 415

His Gly Tyr Arg Gln Cys Val Pro His Asn Asp Asp Thr Thr Val Thr
            420                 425                 430

Pro Leu Pro Ser Leu Ser Phe Ser Ser Gly Tyr Val Gln Arg Ser Ile
        435                 440                 445

Ala Asp Leu Pro Lys Gln Gly Ser Lys Arg Pro Trp Arg Leu Tyr Gln
    450                 455                 460

Asn Tyr Ala Leu Asp Ile Val Ser Leu Arg Phe Gly Lys Val Asp Asp
465                 470                 475                 480

Gly Val Met Arg Tyr Ser
                485


<210> SEQ ID NO 5
<211> LENGTH: 1461
<212> TYPE: DNA
<213> ORGANISM: Artificial Sequence
<220> FEATURE:
<223> OTHER INFORMATION: variation

<400> SEQUENCE: 5

atgtcaactg agcatgtcga cgtgctgatc gtcggtgccg ggctgtccgg catcgccgcc      60

gcctatcatc tgcagcacaa atgtccgggc aagcgcttcg ccctcctgga ggggcgcggt     120

gcgctcggcg gcacctggga cctgttccgc tatcccggca tccgctcgga cagcgacatg     180

tacacgctcg gctattcgtt caagccgtgg accgatccga aagccatcgc cgacgggccg     240

cagatcctca aatatgtcca ggacaccgcg accgagaacg gcatcgaccg ccacatccgt     300

ttcaatcatc gcgtccgccg cgcctcgtgg tcgagcgcgg acgcacgctg gacggtcgag     360

gccgagcggc agacggcgca gggcacgacg gaaaccgtgt cgatgacatg cggcttcctt     420

ttcatgtgct ccggctacta ccgctatgag aaaggctatc tgccggactt caagggcatg     480

gccgatttca agggccgcat cgtgcatccg caggcctggc ccgccgacct cgactatgcc     540

ggcaaacgcg tcgtcgtgat cggctccggt gcgacggcgg tgacgctggt gccggcaatg     600

gccaagaccg cggcgcacgt gacgatgctg cagcgctcgc cgacctatgt cgtgtcgcgc     660

ccggcgcagg atgcgctcgc caacaagctg cgcgagcacc tcccggctgg tctcgcctat     720
```

catctgatcc gctggcgcaa cgtgctgttc gggatgtatt tcttccagct cagccgccgc 780
aagccgcagc gggtcaagca gctgatatta gggggcgtgc gcgccgcgct tggccccgac 840
tacgacgtcg ccacccattt cacgccgcgc tacaacccgt gggaccagcg gttgtgcctg 900
gtgccggatg gcgacctgtt caggaccatc cgcgagcagc gggcgtcggt ggtgacagcc 960
gggatcgaca cgttcaccga gcgcggcctg cgcctctccg acggccgcga gctcgaggcc 1020
gaaatcgtgg tgaccgcgac ggggctggtg ctgcaggttc tcggcggcat cgaggtcgtg 1080
gtcgacggcc gcacggtcga ttttgccaag acgctcaact acaagggcat gatgtattcc 1140
gacgtgccca acatggcggc caccctcggc tacacgaacg catcgtggac gctgaaatgc 1200
gatctcacct gcgaatatgt ctgccgtctc ctcaactaca tggatcgcca tggctatcgc 1260
caatgcgtgc cgcacaacga cgacaccacc gtcacgccgc tgccgtcgct gagcttcagc 1320
tccggctatg tgcagcgctc gattgccgac ctgcccaagc aaggctcgaa gcggccgtgg 1380
cggctgtacc agaactacgc gctggatatc gtctcgctgc ggttcggcaa ggtcgatgat 1440
ggggtgatgc ggtattcgtg a 1461

<210> SEQ ID NO 6
<211> LENGTH: 486
<212> TYPE: PRT
<213> ORGANISM: Artificial Sequence
<220> FEATURE:
<223> OTHER INFORMATION: VARIANT

<400> SEQUENCE: 6

Met Ser Thr Glu His Val Asp Val Leu Ile Val Gly Ala Gly Leu Ser
1 5 10 15

Gly Ile Ala Ala Ala Tyr His Leu Gln His Lys Cys Pro Gly Lys Arg
20 25 30

Phe Ala Leu Leu Glu Gly Arg Gly Ala Leu Gly Gly Thr Trp Asp Leu
35 40 45

Phe Arg Tyr Pro Gly Ile Arg Ser Asp Ser Asp Met Tyr Thr Leu Gly
50 55 60

Tyr Ser Phe Lys Pro Trp Thr Asp Pro Lys Ala Ile Ala Asp Gly Pro
65 70 75 80

Gln Ile Leu Lys Tyr Val Gln Asp Thr Ala Thr Glu Asn Gly Ile Asp
85 90 95

Arg His Ile Arg Phe Asn His Arg Val Arg Arg Ala Ser Trp Ser Ser
100 105 110

Ala Asp Ala Arg Trp Thr Val Glu Ala Glu Arg Gln Thr Ala Gln Gly
115 120 125

Thr Thr Glu Thr Val Ser Met Thr Cys Gly Phe Leu Phe Met Cys Ser
130 135 140

Gly Tyr Tyr Arg Tyr Glu Lys Gly Tyr Leu Pro Asp Phe Lys Gly Met
145 150 155 160

Ala Asp Phe Lys Gly Arg Ile Val His Pro Gln Ala Trp Pro Ala Asp
165 170 175

Leu Asp Tyr Ala Gly Lys Arg Val Val Val Ile Gly Ser Gly Ala Thr
180 185 190

Ala Val Thr Leu Val Pro Ala Met Ala Lys Thr Ala Ala His Val Thr
195 200 205

Met Leu Gln Arg Ser Pro Thr Tyr Val Val Ser Arg Pro Ala Gln Asp
210 215 220

-continued

```
Ala Leu Ala Asn Lys Leu Arg Glu His Leu Pro Ala Gly Leu Ala Tyr
225                 230                 235                 240

His Leu Ile Arg Trp Arg Asn Val Leu Phe Gly Met Tyr Phe Phe Gln
                245                 250                 255

Leu Ser Arg Arg Lys Pro Gln Arg Val Lys Gln Leu Ile Leu Gly Gly
            260                 265                 270

Val Arg Ala Ala Leu Gly Pro Asp Tyr Asp Val Ala Thr His Phe Thr
        275                 280                 285

Pro Arg Tyr Asn Pro Trp Asp Gln Arg Leu Cys Leu Val Pro Asp Gly
    290                 295                 300

Asp Leu Phe Arg Thr Ile Arg Glu Gln Arg Ala Ser Val Val Thr Ala
305                 310                 315                 320

Gly Ile Asp Thr Phe Thr Glu Arg Gly Leu Arg Leu Ser Asp Gly Arg
                325                 330                 335

Glu Leu Glu Ala Glu Ile Val Val Thr Ala Thr Gly Leu Val Leu Gln
            340                 345                 350

Val Leu Gly Gly Ile Glu Val Val Val Asp Gly Arg Thr Val Asp Phe
        355                 360                 365

Ala Lys Thr Leu Asn Tyr Lys Gly Met Met Tyr Ser Asp Val Pro Asn
    370                 375                 380

Met Ala Ala Thr Leu Gly Tyr Thr Asn Ala Ser Trp Thr Leu Lys Cys
385                 390                 395                 400

Asp Leu Thr Cys Glu Tyr Val Cys Arg Leu Leu Asn Tyr Met Asp Arg
                405                 410                 415

His Gly Tyr Arg Gln Cys Val Pro His Asn Asp Asp Thr Thr Val Thr
            420                 425                 430

Pro Leu Pro Ser Leu Ser Phe Ser Ser Gly Tyr Val Gln Arg Ser Ile
        435                 440                 445

Ala Asp Leu Pro Lys Gln Gly Ser Lys Arg Pro Trp Arg Leu Tyr Gln
    450                 455                 460

Asn Tyr Ala Leu Asp Ile Val Ser Leu Arg Phe Gly Lys Val Asp Asp
465                 470                 475                 480

Gly Val Met Arg Tyr Ser
                485


<210> SEQ ID NO 7
<211> LENGTH: 27
<212> TYPE: DNA
<213> ORGANISM: Artificial Sequence
<220> FEATURE:
<223> OTHER INFORMATION: Forward primer

<400> SEQUENCE: 7

ccgcatatgt caactgagca tgtcgac                                          27


<210> SEQ ID NO 8
<211> LENGTH: 29
<212> TYPE: DNA
<213> ORGANISM: Artificial Sequence
<220> FEATURE:
<223> OTHER INFORMATION: Reverse primer

<400> SEQUENCE: 8

ccgaagcttt cacgaatacc gcatcaccc                                        29
```